US005725521A

United States Patent [19]

Mueller

[11] Patent Number: 5,725,521
[45] Date of Patent: Mar. 10, 1998

[54] DEPTH STOP APPARATUS AND METHOD FOR LASER-ASSISTED TRANSMYOCARDIAL REVASCULARIZATION AND OTHER SURGICAL APPLICATIONS

[75] Inventor: Richard L. Mueller, Sunnyvale, Calif.

[73] Assignee: Eclipse Surgical Technologies, Inc., Sunnyvale, Calif.

[21] Appl. No.: 627,701

[22] Filed: Mar. 29, 1996

[51] Int. Cl.$^6$ .................................................... A61B 17/36
[52] U.S. Cl. .................................................... 606/7; 606/15
[58] Field of Search ........................... 128/665, 660.03; 607/89; 606/1, 2, 2.5, 7, 10, 14, 15, 16, 17

[56] References Cited

U.S. PATENT DOCUMENTS

| 4,658,817 | 4/1987 | Hardy | 128/303.1 |
|---|---|---|---|
| 4,976,710 | 12/1990 | Mackin | |
| 4,997,435 | 3/1991 | Demeter | 606/2.5 X |
| 4,998,972 | 3/1991 | Chin et al. | |
| 5,026,366 | 6/1991 | Leckrone | 607/87 X |
| 5,125,926 | 6/1992 | Rudko et al. | 606/19 |

(List continued on next page.)

FOREIGN PATENT DOCUMENTS 0542428  10/1992  European Pat. Off.

OTHER PUBLICATIONS

Deckelbaum, "Cardiovascular Apps. of Laser Tech.", Lasers in Surgery and Medicine. 15:315–341 (1994).

Frazier et al., "Myocard. Revasc. with Las.", Cullen Cardio. Res. Labs., Tx. Heart Inst., Supp. II C vol 92, No. 9, II-58–65 (Nov. 1, 1995).

LeNatles, Jeffrey "Fiberoptic Laser Catheter . . . ", WO 92/02276 20 Feb. 1992 (Copy 607/89).

Jovier, M.A. et al "Surgical Channel Forming Device With Penetration Limiter", Published PCT Intnl Appln WO 96/39965 published 19 Dec. 1996 from PCT Appln No. PCT/US96/09160.

*Primary Examiner*—Francis Jaworski
*Attorney, Agent, or Firm*—Ray K. Shahani; Christopher N. Sears

[57] ABSTRACT

Improved methods and apparatuses related to laser-assisted transmyocardial revascularization, and more particularly, to improved methods and apparatuses for precisely positioning a fiber-optic or other waveguide adjacent the area or areas to be lased, including at positions adjacent the posterior epicardial and endocardial surfaces of the heart and at transseptal positions within the chambers of the heart, thereby making possible the creation of channels in myocardial tissue at precisely the positions in the heart where ischemia or infarction or other have rendered such treatment desirable or necessary. These methods and apparatuses can be adapted for use in surgical applications throughout the human body or in animals for transmitting laser energy precisely, at predetermined positions and to predetermined depths. A catheter device for performing laser-assisted transmyocardial revascularization (TMR), the device particularly adapted for delivery of laser energy via a laser delivery device or manipulation of some other apparatus inside a body cavity or organ chamber where the depth of delivery of the laser energy is critical to the procedure, the device comprising an outer lumen and a depth stop, the depth stop having a deploying device, such that when the catheter device is placed adjacent tissue to be lased and the depth stop is deployed, the spatial reference of the position of the catheter device and the laser delivery device or other apparatus used in the catheter device is maintained in a predetermined position relative to the position of the distal end of the outer lumen. Deployment of the depth stop consists of inflating a balloon tip, or there may also be an inner lumen such that deployment comprises slightly retracting the inner lumen such that an expanding mechanism such as a braided basket or "moly bolt" device increases the diameter of the end of the catheter device, thereby providing a contacting surface for performing the surgical procedure, whether it be laser ablation, visualization, or other. A method of use is also described.

25 Claims, 5 Drawing Sheets

U.S. PATENT DOCUMENTS

| | | | |
|---|---|---|---|
| 5,188,635 | 2/1993 | Radtke | 607/7 X |
| 5,380,316 | 1/1995 | Aita et al. | 606/7 |
| 5,389,096 | 2/1995 | Aita et al. | 606/15 |
| 5,454,782 | 10/1995 | Perkins | 607/89 X |
| 5,578,007 | 11/1996 | Imran | 607/15 X |
| 5,593,405 | 1/1997 | Osypka | 606/15 |
| 5,607,421 | 3/1997 | Jeevanandam et al. | 606/7 X |
| 5,643,253 | 7/1997 | Baxter et al. | 606/7 X |

DEPTH STOP APPARATUS AND METHOD FOR LASER-ASSISTED TRANSMYOCARDIAL REVASCULARIZATION AND OTHER SURGICAL APPLICATIONS

RELATED APPLICATIONS

This application is filed concurrently with U.S. patent application Ser. No. 08/627,704 and U.S. patent application Ser. No. 08/677,699, which applications are expressly incorporated herein in their entirety

FIELD OF THE INVENTION

The present invention relates to the surgical procedure known as laser-assisted transmyocardial revascularization (TMR), and more particularly, to improved methods and apparatuses for precisely positioning a fiber-optic or other waveguide adjacent the area or areas to be lased, including at positions adjacent the posterior epicardial and endocardial surfaces of the heart and at trans-septal positions within the chambers of the heart, thereby making possible the creation of channels in myocardial tissue at precisely the positions in the heart where ischemia or infarction or other have rendered such treatment desirable or necessary. These methods and apparatuses can be adapted for use in surgical applications throughout the human body or in animals for transmitting laser energy precisely, at predetermined positions and to predetermined depths.

BACKGROUND OF THE INVENTION

Figure 1:
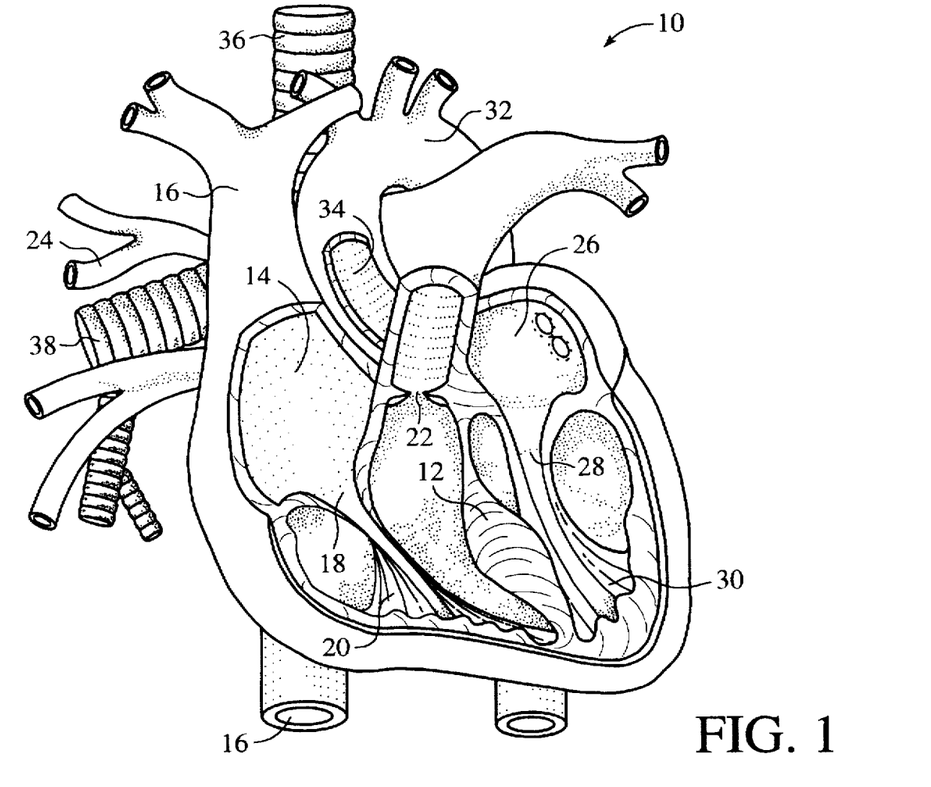
FIG. 1 is a schematic view of the human heart.

FIG. 1 is a schematic view of the human heart. The human heart 10 is a muscular dual pump that beats continuously throughout life sending blood to the lungs and the rest of the body. The interior of the heart consists of four distinct chambers. The septum 12, a thick central muscular wall, divides the cavity into fight and halves. On the right side, the upper half is known as the fight atrium 14. Deoxygenated blood from the rest of the body arrives in the right atrium via the vena cava 16, the blood is pumped across a one-way valve known as the tricuspid valve 18 into the lower portion known as the right ventricle 20. From there the blood circulates to the lungs through the pulmonary valve 22 via the pulmonary artery 24 where it is oxygenated by circulation through the alveoli of the lungs (not shown). The blood returns via the pulmonary veins to the left atrium 26 and flows through a second valve, the mitral valve 28 into the left ventricle 30 where it is pumped via the aorta 32 to the rest of the body.

Much of the heart consists of a special type of muscle called myocardium. The myocardium requires a constant supply of oxygen and nutrients to allow it to contract and pump blood throughout the vasculature. The inner surfaces of the chambers of the heart are lined with a smooth membrane, the endocardium, and the entire heart is enclosed in a tough, membranous bag known as the pericardial sac.

The pumping action of the heart has three main phases for each heart beat. Diastole is the resting phase during which the heart fills with blood: while deoxygenated blood is entering the right atrium oxygenated blood is returned from the lungs to the left atrium. During the atrial systole, the two atria contract simultaneously, squeezing the blood into the lower ventricles. Finally, during ventricular systole the ventricles contract to pump the deoxygenated blood into the pulmonary arteries and the oxygenated blood into the main aorta. When the heart is empty, diastole begins again. The electrical impulses which stimulate the heart to contract in this manner emanate from the heart's own pacemaker, the sinoatrial node. The heart rate is under the external control of the body's autonomic nervous system.

Figure 2:
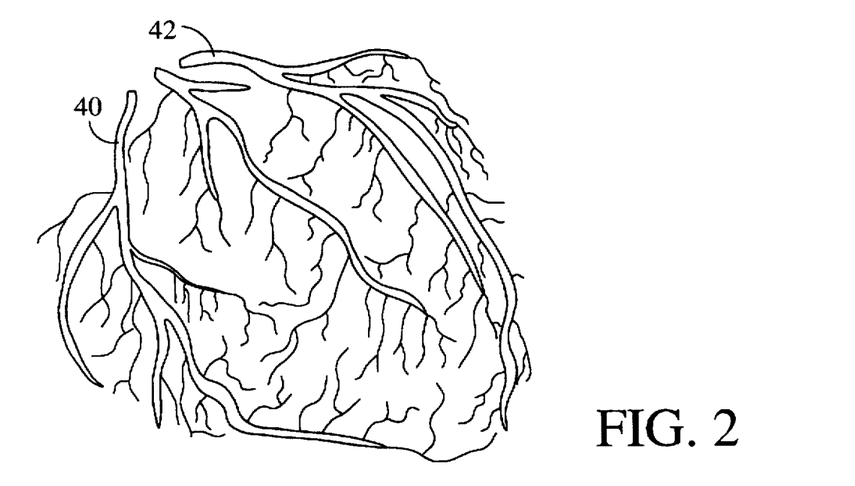
FIG. 2 is a schematic view of the coronary arteries on the outer surface of the human heart.

FIG. 2 is a schematic view of the coronary arteries on the outer surface of the human heart. Though the heart supplies blood to all other parts of the body, the heart itself has relatively little communication with the oxygenated blood supply. Thus, the two coronary arteries, the left coronary artery 40 and the fight coronary artery 42 which arise from the aorta and encircle the heart muscle on either side "like a crown" to supply the heart itself with blood.

Heart disorders are a common cause of death in developed countries. They also impair the quality of life of millions of people restricting activity by causing pain, breathlessness, fatigue, fainting spells and anxiety. The major cause of heart disease in developed countries is impaired blood supply. The coronary arteries, which supply blood to the heart, become narrowed due to atherosclerosis and parts of the heart muscle are deprived of oxygen and other nutrients. The resulting ischemia or blockage can lead to angina pectoris, a pain in the chest, arms or jaw due to a lack of oxygen to the heart, or infarction, death of an area of the myocardium caused by the ischemia.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be relieved in a number of ways. Drug therapy, including nitrates, beta-blockers, and peripheral vasodilator drugs (to dilate the arteries) or thrombolytic drugs (to dissolve the clot) can be very effective. If drug treatment fails transluminal angioplasty is often indicated—the narrowed part of the artery, dogged with atherosclerotic plaque or other deposits, can be stretched apart by passing a balloon to the site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as coronary artery bypass grafting (CABG) may be indicated. CABG is the most common and successful major heart operation performed, in America alone over 500,000 procedures being performed annually. The procedure takes at least two surgeons and can last up to five hours. First, the surgeon makes an incision down the center of the patient's chest and the heart is exposed by opening the pericardium. A length of vein is removed from another part of the body, typically the leg. The patient is connected to a heart-lung machine which takes over the function of the heart and lungs during the operation. The section of veto is first sewn to the aorta and then sewn onto the coronary artery at a point such that oxygenated blood can flow directly into the heart. The patient is then closed. Not only does the procedure require the installation of the heart-lung machine, a very risky procedure, but the sternum must be sawed through and the risk of infection is enhanced during the time the chest cavity is spread open.

Another method of improving myocardial blood supply is called transmyocardial revascularization (TMR), the creation of channels from the epicardial to the endocardial portions of the heart. The procedure using needles in a form of "myocardial acupuncture" has been experimented with at least as early as the 1930s and used clinically since the 1960s. Deckelbaum. L. I., Cardiovascular Applications of Laser technology, *Lasers in Surgery and Medicine* 15:315–341 (1994). The technique was said to relieve ischemia by allowing blood to pass from the ventricle through the channels either directly into other vessels perforated by the channels or into myocardial sinusoids which connect to the myocardial microcirculation. The procedure has been likened to transforming the human heart into one resembling that of a reptile.

In the reptile heart, perfusion occurs via communicating channels between the left ventricle and the coronary arteries. Frazier, O. H., Myocardial Revascularization with Laser— Preliminary Findings, *Circulation*, 1995; 92 [suppl II]:II-58–II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous studies have been performed on TMR using lasers to bore holes in the myocardium. The exact mechanism by which blood flows into the myocardium is not well understood however. In one study, 20–30 channels per square centimeter were bored into the left ventricular myocardium of dogs prior to occlusion of the arteries. LAD ligation was conducted on both the revascularized animals as wall as a set of control animals. Results showed that animals having undergone TMR prior to LAD ligation acutely showed no evidence of ischemia or infarction in contrast to the control animals. After sacrifice of the animals at ages between 4 weeks and 5 months, the laser-created channels could be demonstrated grossly and microscopically to be open and free of debris and scarring.

It is believed that the TMR channels occlude toward the epicardial surface but that their subendocardial section remains patent (unobstructed) and establishes camerosinusoidal connections. It is possible that the creation of laser channels in the myocardium may promote long-term changes that could augment myocardial blood flow such as by inducing angiogenesis in the region of the lased (and thus damaged) myocardium. Support of this possibility is reported in histological evidence of probable new vessel formation adjacent to collagen occluded transmyocardial channels. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the lumen of the laser channels is or can become hemocompatible and that it resists occlusion caused by thrombo-activation and/or fibrosis. A thin zone of charring occurs on the periphery of the laser-created transmyocardial channels through the well-known thermal effects of optical radiation on cardiovascular tissue. This type of interface may inhibit the immediate activation of the intrinsic clotting mechanisms because of the inherent hemocompatibility of carbon. In addition, the precise curing action that results from the high absorption and low scattering of laser energy ($CO_2$, HO, etc.) may minimize structural damage to collateral tissue, thus limiting the tissue thromboplastin-mediated activation of the extrinsic coagulation.

U.S. Pat. No. 4,658,817 issued Apr. 21, 1987 to Hardy teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforated a portion of tissue to provide the laser beam direct access to distal tissue.

U.S. Pat. No. 5,125,926 issued Jun. 30, 1992 to Rudko et al. teaches a heart-synchronized pulsed laser system for TMR. The device and method comprises a device for sensing the contraction and expansion of a beating heart. As the heart beat is monitored, the device triggers a pulse of laser energy to be delivered to the heart during a predetermined portion of the heartbeat cycle. This heart-synchronized pulsed laser system is important where the type of laser, the energy and pulse rate are potentially damaging to the beating heart or it's action. Often, application of laser energy to a beating heart can induce fibrillation or arrhythmia. Additionally, as the heart beats, it's spatial relationship between the heart and the tip of the laser delivery probe may change so that the necessary power of the beam and the required position of the handpiece may be unpredictable.

Finally, U.S. Pat. No. 5,380,316 issued Jan. 10, 1995 and U.S. Pat. No. 5,389,096 issued Feb. 14, 1995 both to Aita et al. teach systems and methods for intra-operative and percutaneous myocardial revascularization, respectively. The former patent is related to TMR performed by inserting a portion of an elongated flexible lasing apparatus into the chest cavity of a patient and lasing channels directly through the outer surface of the epicardium into the myocardium tissue. In the latter, TMR is performed by guiding an elongated flexible lasing apparatus into a patient's vasculature such that the firing end of the apparatus is adjacent the endocardium and lasing channels directly through the endocardium into the myocardium tissue without perforating the epicardial layer or even the pericardium. These patents do not teach any method for controlling the elongated flexible laser delivery apparatus, nor do they teach methods of visualizing the areas of the heart being lased nor do they teach any method or devices for achieving TMR on surfaces or portions of the heart which are not directly accessible via a sternotomy, mini-sternotomy or via a trocar.

TMR is most often used to treat the lower left chamber of the heart. The lower chambers or ventricles are serviced by the more distal branches of the coronary arteries. Distal coronary arteries are more prone to blockage and resulting heart muscle damage. Roughly 50% of the left ventricle is direct line accessible through a thoracotomy or small incision between the ribs. However, roughly 50% is not direct line accessible and requires either rotating the heart or sliding around to the back side of the heart. Access to the heart is achieved cy (1) sliding a device between the heart and pericardial sack which encases the heart, the device likely to have a 45–90 degree bend near the tip, (2) lifting the still beating heart, and (3) penetrating through the direct access side of the heart and/or through the septum of the heart. Lifting the still beating heart is less than desirable especially in patients with lowered heart performance. Furthermore, such manipulation can cause tachycardia (rapid beating of the heart absent undue exertion) fibrillation, arrhythmia or other interruptions in the normal beating cycle.

Thus, broadly, it is an object of the present invention to provide an improved method and device for laser-assisted TMR.

It is a further object of the present invention to provide an improved method and device for laser-assisted TMR in which the procedure may be carried out from within the interior of the heart and in which visualization or positioning of the laser delivery means is done by improved means.

It is a further object of the present invention to provide an improved method and device for laser-assisted TMR in which the procedure may be carried out on rear surfaces and other visually hidden external surfaces of the heart and in which visualization or positioning of the laser delivery means is done by improved means.

It is a further object of the present invention to provide an improved method and device for laser-assisted TMR in which the need for visualization during the procedure is minimized by employing a depth stop, such as a mesh basket or "moly bolt" device adjacent the end of the elongated flexible laser delivery means, to position the distal end of the laser delivery means It is a further object of the present invention to provide an improved method and device for laser-assisted TMR in which the distal end of the elongated flexible laser delivery means comprises a known visualization system with an adjunct visualization device to enhance the quality of the visualized image.

It is a further object of the present invention to provide an improved method and device for laser-assisted TMR in which the need for visualization during the procedure is minimized by deploying a mechanical or other tether coupled to the heart at a point adjacent to the area to be revascularized, thereby conveying the distal end of the laser delivery means to that area and maintaining it in a predetermined position during the creation of channels within the tissue of the myocardium.

SUMMARY OF THE INVENTION

A surgical device for performing laser-assisted transmyocardial revascularization (TMR), the device particularly adapted for delivery of laser energy via a laser delivery means or manipulation of some other apparatus inside a body cavity or organ chamber where the depth of delivery of the laser energy is important to the procedure, the device comprising an outer lumen, the outer lumen ("lumen" is shorthand for referencing a structural sleeve member in this specification) having a proximal end and a distal end, the outer lumen defining the central axis of the surgical device, a depth stop, the depth stop disposed at a point on the outer lumen adjacent the distal end of the outer lumen, the depth stop having a deploying means, such that when the surgical device is placed adjacent tissue to be lased and the depth stop is deployed, the spatial reference of the position of the surgical device and the laser delivery means or other apparatus used in the surgical device is maintained in a predetermined position relative to the position of the distal end of the outer lumen. In a preferred embodiment, the surgical device is adapted for use as a catheter device, the catheter device useful for use in vascular channels and organ chambers. In a preferred embodiment, the distal end of the outer lumen extends slightly past the depth stop thereby providing a distally extending end portion. In a preferred embodiment, the distally extending end portion is tapered and able to penetrate tissue. In a preferred embodiment the distally extending end portion is mechanically sharpened. In a preferred embodiment the outer lumen is rigid. In a preferred embodiment the outer lumen is flexible. In a preferred embodiment the depth stop comprises a balloon tip such that deployment of the depth stop consists of inflating the balloon tip. In a preferred embodiment there is also an inner lumen, the inner lumen disposed inside the outer lumen, the inner lumen having a proximal end and a distal end, the distal end connected to the distal end of the outer lumen. In a preferred embodiment the depth stop comprises a braided basket such that deployment of the depth stop consists of a slight retraction of the inner lumen within the outer lumen such that the depth stop is compressed axially and expanded radially. In a preferred embodiment the depth stop comprises a moly bolt tip such that deployment consists of causing the moly bolt to develop radial protrusions. In a preferred embodiment there is a depth stop deploying mechanism. In a preferred embodiment there is a depth stop deploying mechanism, the proximal ends of the outer and the inner lumens connected to the mechanism, the mechanism having a control means, the control means able to cause the depth stop mechanism to be deployed. In a preferred embodiment the depth stop further comprises a contacting surface essentially perpendicular to the central axis of the catheter device. In a preferred embodiment there is a laser delivery means, the laser delivery means disposed inside the outer lumen. In a preferred embodiment there is a distally extending tip portion extending axially past the depth stop, the distally extending tip portion having a plurality of openings such that a plurality of laser delivery means introduced into the outer lumen can be extended through the surgical device through the distal end of the outer lumen for the delivery of laser energy therefrom. In a preferred embodiment there is a plunger the plunger extending parallel with the central axis of the surgical device and through the outer lumen, the plunger having a proximal end and a distal end. In a preferred embodiment there is a mechanical linkage element, the mechanical linkage attached to the distal end of the outer lumen at a point of attachment, the mechanical linkage element having a cam surface, the mechanical linkage element further having a distally extending redirecting surface, such that when the plunger is moved axially through the outer lumen such that it's distal end is brought to bear against the cam surface, the mechanical linkage dement is rotated about the point of attachment between the mechanical linkage element and the distal end of the outer lumen, thereby redirecting a laser delivery means extending through the outer lumen of the surgical device to an angle with respect to the central axis of the surgical device for precise control of the delivery of laser energy.

A method of using a surgical or catheter device with depth stop for performing laser-assisted transmyocardial revascularization (TMR), the device particularly adapted for delivery of laser energy via a laser delivery means or manipulation of some other apparatus inside a body cavity or organ chamber, the method comprising the following steps: (a) positioning the distal end of a surgical or catheter device with depth stop adjacent the subject tissue; (b) deploying the depth stop so as to maintain a precise spatial relationship between the surgical or catheter device and the subject tissue; (c) positioning a laser energy delivery device via the surgical or catheter device adjacent the subject tissue to be lased; and (d) delivering a predetermined amount of laser energy to the subject tissue. In a preferred embodiment, during step (d), the laser energy is delivered to a portion of the human heart to be revascularized by TMR thereby creating channels in the subject tissue extending a predetermined distance into the subject tissue, thus providing the surgeon with a high degree of control, in particular allowing the surgeon to revascularize tissue from within a body cavity or from within an organ chamber and create channels in the subject tissue without perforating or penetrating the subject tissue or organ completely. In a preferred embodiment, prior to delivery of laser energy, the distally extending tip portion of the distal end of the surgical or catheter device is pushed into the tissue adjacent the area to be revascularized. In a preferred embodiment, the following step is taken: (e) delivering a predetermined amount and type of material to the subject tissue, the material being one of those selected from the group consisting of antibiotics to prevent infection of the TMR channels, blood thinning agents, other heart-function modifiers or visualization or marking means.

A method of performing TMR in which a surgical or catheter device is placed into position and maintained there precisely, the surgical or catheter device having a depth stop such that once the surgical or catheter is placed and the depth stop is deployed the catheter device will maintain its spatial relationship with the tissue to be lased, the method comprising the following steps: (a) placing a surgical or catheter device with an expandable depth stop mechanism into a body cavity or organ chamber; (b) deploying the depth stop mechanism to expand the depth stop mechanism such that one or more essentially perpendicular surfaces of the depth stop are brought to bear against an internal surface of the body cavity or against an internal or external surface of an organ chamber; (c) maintaining the spatial relationship between the surgical or catheter device and the tissue to be lased; (d) delivering laser energy to the subject tissue such that TMR channels are created in the tissue to be lased; (e) disengaging the depth stop mechanism; and (f) retracting the surgical or catheter device. In a preferred embodiment the surgical or catheter device is placed through an external surface of the human heart so that the distal end of the surgical or catheter device is disposed inside heart during step (a), the deployed depth stop mechanism of the surgical or catheter device is repositioned such that a perpendicular contacting surface of the depth stop is brought to bear against the inside surface of the heart chamber during step (c), and the TMR channels created by the laser energy extend from the inside surface of the heart chamber toward the outer surface of the heart through a portion of the myocardium during step (d). In a preferred embodiment the surgical or catheter device is placed through an external surface of the human heart so that the distal end of the surgical or catheter device is disposed inside the heart adjacent the distally located endocardium surface during step (a), the deployed depth stop mechanism of the surgical or catheter device is repositioned such that a perpendicular contacting surface of the depth stop is brought to bear against the distally located endocardium surface of the heart chamber during step (c), and the TMR channels created by the laser energy extend from the distally located endocardium surface of the heart chamber toward the outer surface of the heart through a portion of the myocardium during step (d). In a preferred embodiment the surgical or catheter device is placed vascularly into the human heart so that the distal end of the surgical or catheter device is disposed inside a heart chamber adjacent the distally located endocardium surface during step (a), the deployed depth stop mechanism of the catheter device is repositioned such that a perpendicular contacting surface of the depth stop is brought to bear against the distally located endocardium surface of the left ventricle chamber during step (c), and the TMR channels created by the laser energy extend from the distally located endocardium surface of the heart chamber toward the outer surface of the hem through a portion of the myocardium during step (d).

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE PREFERRED EMBODIMENT

Figure 3:
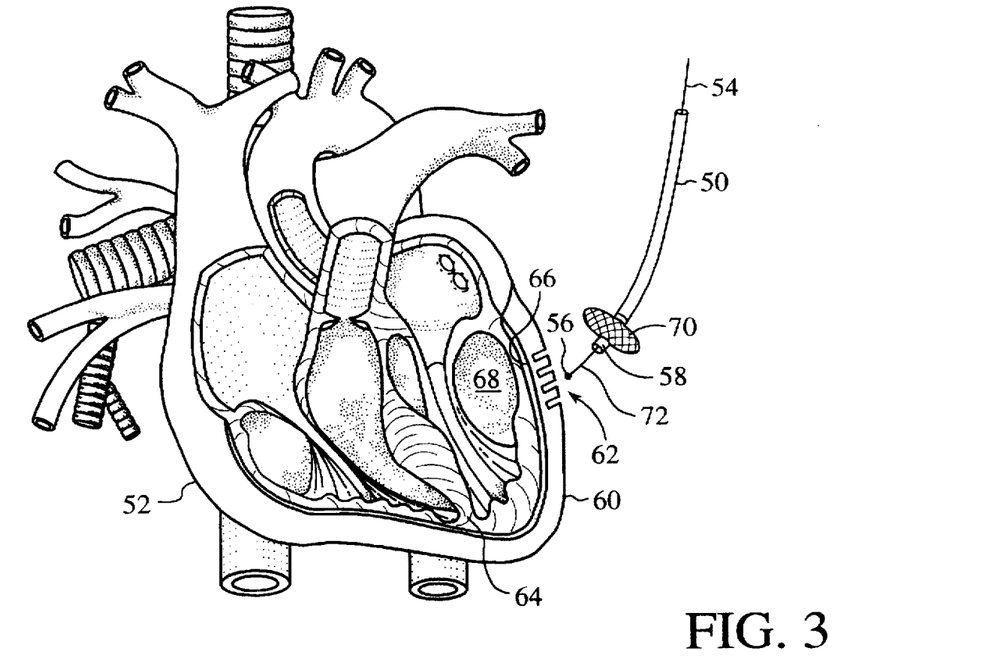
FIG. 3 is a cross section view of the human heart demonstrating a preferred method of TMR from the epicardium of the present invention.

FIG. 3 is a cross section view of the human heart demonstrating a preferred method of TMR from the epicardium of the present invention. As is wall known in surgical methodology, the heart can be accessed externally via a mini-sternotomy perhaps with the use of a trocar or some other insertion tube device. The field of microsurgery is advancing rapidly and small sophisticated tools can be introduced into the chest cavity. These devices include visualization probes, such as a 2-millimeter fiber bundle, laser delivery means, and other accessories including dye swabs, guide-wire tethers, additional illumination means, etc. In FIG. 3, a surgical device is described. It will be understood that in the present disclosure of the preferred embodiments of the present invention, a "surgical device" is distinguished from a "catheter device". The former term will be used to describe instruments which access the heart via an external opening made in the chest or elsewhere whereas the latter will be used to refer to instruments used in vascular channels or organ chambers.

Once the lumen 50 of the surgical device has passed through the pericardial sac, not shown, via an incision or other perforation, it is positioned adjacent the epicardial surface 52 of the heart. The laser delivery means 54, optionally fiber optic or other waveguide structure, extends therethrough with the distal end 56 of the laser delivery means located near the distal end 58 of the outer lumen. As the laser energy is delivered to the adjacent epicardial surface 59, micro-channels 62 are produced in the epicardial surface, extending into the myocardium tissue 64 but not penetrating the interior endocardium surface 66 of the chamber 68, in front of the laser beam.

In a preferred embodiment, a depth stop device 70 is located near the distal end of the surgical device and is deployed as soon as the advancing distal end of the outer lumen of the surgical device is adjacent the area to be lased. Once the depth stop device is deployed, as will be more fully described below, a short, predetermined length 72 of the distal end of the outer lumen extends slightly forward of the depth stop device. This short extending length of outer lumen can be pushed into the epicardial surface by lasing or by sharpened or other mechanical, piercing means. In this fashion, the depth stop will allow the tip of the surgical device to be extended a precise distance into the epicardium, and revascularization channeling can be initiated from this surface a predetermined distance into the myocardium tissue without fear of penetrating the interior endocardium surface.

Figure 4:
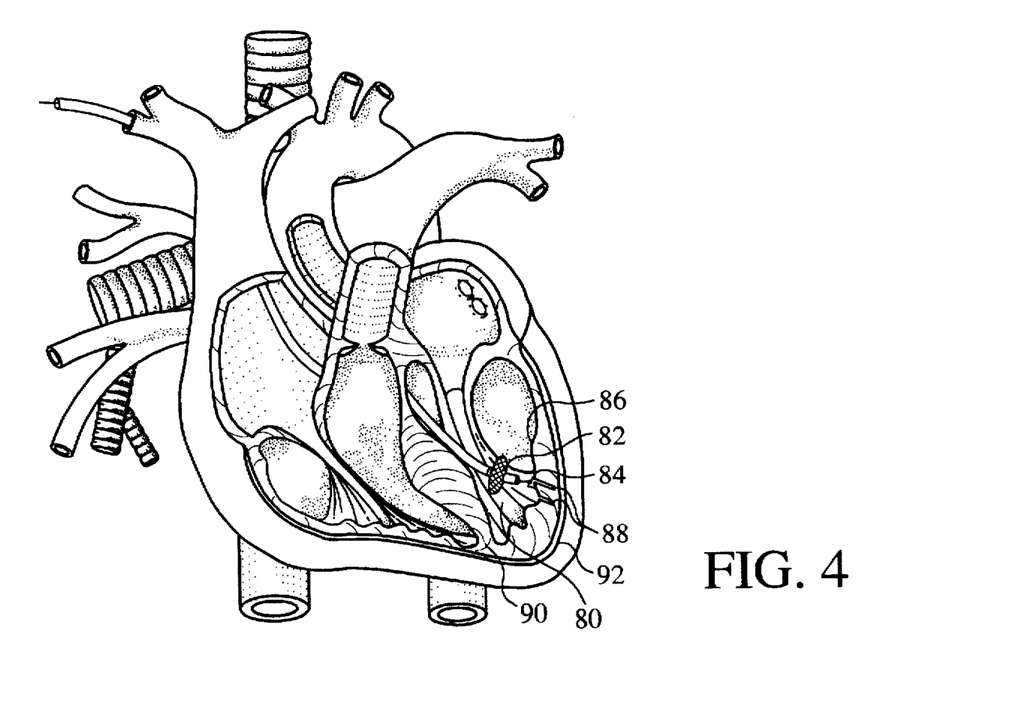
FIG. 4 is a cross section view of the human heart demonstrating a preferred method of TMR from the endocardium of the present invention.

FIG. 4 is a cross section view of the human heart demonstrating a preferred method of TMR from the endocardium of the present invention. In this procedure, the left ventricle 80 is internally accessed via the aorta by the catheter device 82, perhaps introduced via the femoral artery or otherwise. The laser delivery 84 device within the typically flexible catheter is positioned adjacent the endocardium surface 86. Micro-channels 88 are lased into the myocardium tissue 90 but do not perforate the epicardial surface 92. It will be understood that, as in the prior embodiments, a depth stop device can be positioned at the distal end of the outer lumen of the catheter device. By providing a short extending tip portion of the outer lumen slightly in advance of the depth stop, a precisely controllable system for piercing the endocardium surface at predetermined positions and optimum distances is available. The TMR channels created will extend only as far as desired, starting from the interior endocardium surface into the myocardium without extending to the epicardial surface and thereby risking perforation of a coronary artery.

It will be understood by those skilled in the art of cardiac catheterization and other surgical procedures that once the distal tip of the laser delivery means pierces or otherwise penetrates the myocardium and the depth stop device is deployed, advancing the laser delivery means too far and piercing through an inner chamber, the epicardial surface or a coronary artery will no longer be a problem. The distance between the depth stop device and the very farthest tip of the laser delivery means will be set at safely to ensure that the heart is never pierced too deeply. Further, it has been observed that the thickness changes of the tissue being penetrated between the diastole and the systole phases, to the extent there are significant changes in the thickness of the myocardium itself, the internal endocardium or the epicardial surface, are not significant enough to cause undesirable effects during delivery of laser energy.

Figure 5A:
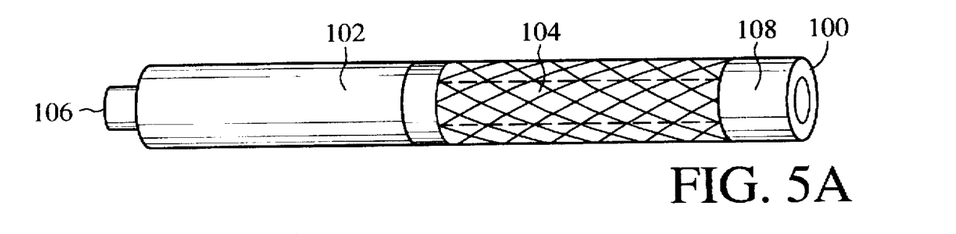
FIG. 5A is a schematic view of a preferred embodiment of a braided basket-type depth stop of the present invention for trans-septal TMR and other procedures performed without the aid of direct visualization.

FIG. 5A is a schematic view of a preferred embodiment of a braided basket-type depth stop of the present invention for trans-septal TMR and other procedures performed without the aid of direct visualization. At the distal end 100 of the device 102 a braided basket portion 104 is provided. It will be understood by those skilled in the art that this braided basket could be made of stainless steel, nylon or some other polymeric material, rubber, etc. It could also be replaced with an equivalently functioning structure, including a transversely fibbed, accordion-like collapsible insert, etc. An inner lumen 106 is located freely inside the catheter device.

Figure 5B:
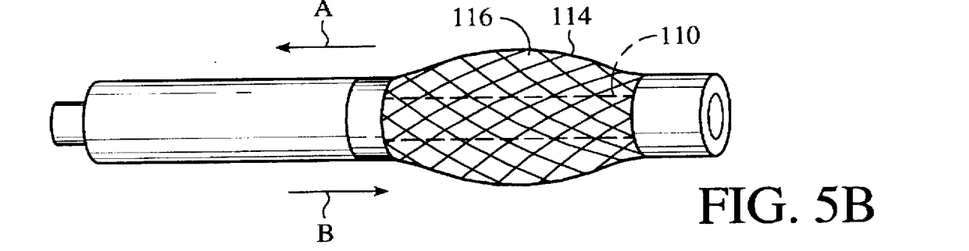
FIG. 5B is a schematic view of a preferred embodiment of a slightly expanded braided basket-type depth stop of the present invention.

FIG. 5B is a schematic view of a preferred embodiment of a slightly expanded braided basket-type depth stop of the present invention. An inner lumen 110 is attached to the distal end of the outer lumen of the device but it is free to slide throughout the rest of the length of the outer lumen 112. As the inner lumen 110 is withdrawn in the direction A, the braided basket portion 114 begins to expand in diameter near points 116. As the inner lumen is moved in the direction B the braided basket portion 114 will contract.

Figure 5C:
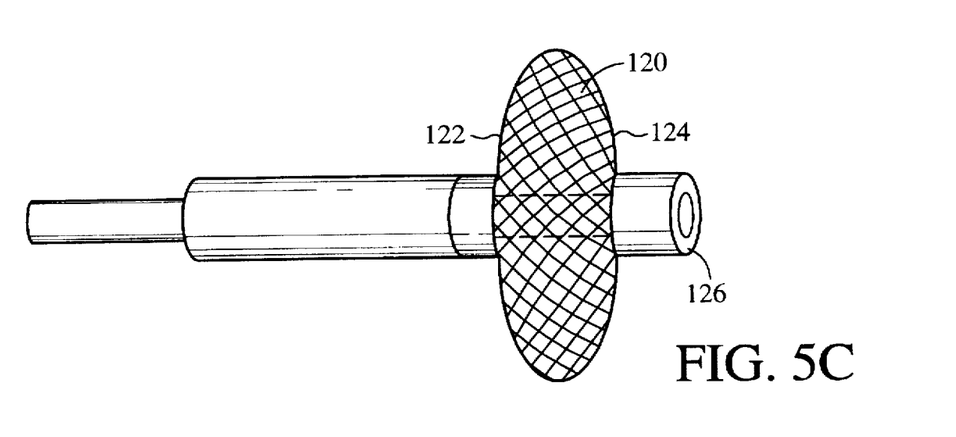
FIG. 5C is a schematic view of a preferred embodiment of a more fully expanded braided basket-type depth stop and extending laser delivery means of the present invention.

FIG. 5C is a schematic view of a preferred embodiment of a more fully expanded braided basket-type depth stop and extending laser delivery means of the present invention. In this view, the braided basket portion 120 is nearly fully expanded in diameter. The proximal perpendicular surface 122 and the distal perpendicular surface 124 are the surfaces which provide an accurate depth stop for surfaces not visually apparent. The distal end 126 of the device is fixed in spatial orientation with the laser delivery means 128 which can be extended and withdrawn independently within the inside of the inner lumen.

Figure 5D:
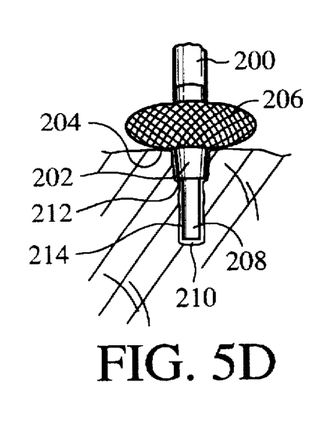
FIG. 5D is a detail cross of a preferred embodiment of the surgical or catheter device of the present invention.

FIG. 5D is a detail cross of a preferred embodiment of the surgical or catheter device of the present invention. Adjacent the distal end of the outer lumen 200, a short distal portion 202 of the outer lumen extends beyond the distal perpendicular contacting surface 204 of the depth stop device 206, shown deployed and in position. The laser delivery means 208 extends therefrom and creates TMR channel 210. In a preferred embodiment, drug delivery can be effectively achieved. Introduced through the outer lumen, optionally between the outer lumen and the laser delivery means, a drug or other substance can be introduced into the TMR channel through a drug delivery port 212. In this manner, various drugs including antibiotics to prevent infection of the TMR channels, blood thinning agents, other heart-function modifiers or visualization or marking means may be introduced to the channel sites.

Figure 6A:
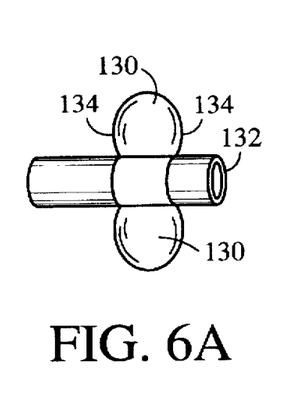
FIG. 6A is a schematic view of a preferred embodiment of a ballooning tip-type depth stop of the present invention.

FIG. 6A is a schematic view of a preferred embodiment of a ballooning tip-type depth stop of the present invention. This is another type of depth stop which can be employed in the method of the present invention. The surgical or catheter device is equipped with one or more ballooning portions 130 near the distal end 132 of the catheter device. It will be understood that once the laser delivery means is positioned inside the surgical or catheter device, it will extend from the distal end of the device as desired by the surgeon. Once the surgical or catheter device is assembled and inserted in the chest cavity, the balloon portions 130 can be inflated with a suitable gas or liquid. It will be understood that the ballooning tip-type depth stop may be more appropriate but less robust in certain circumstances. Proximal and distal perpendicular surfaces 134 will precisely locate the distal end of the device.

Figure 6B:
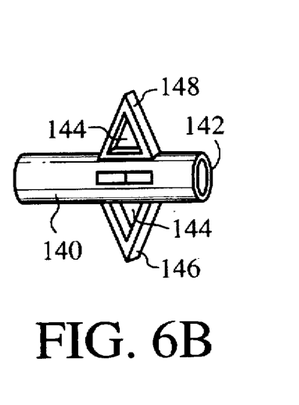
FIG. 6B is a schematic view of a preferred embodiment of a "moly bolt"-type depth stop of the present invention.

FIG. 6B is a schematic view of a preferred embodiment of a "moly bolt"-type depth stop of the present invention. In the view, though not shown, an inner lumen portion is disposed within an outer lumen 140. The inner lumen, attached to the distal end 142 of the outer lumen, once retracted, will cause the remaining material from indentation or removed sections 144 to buckle outward and cause protrusions 146 to form in a radial fashion about the diameter of the outer lumen 140. It will be understood that the laser delivery means would be located precisely with regard to the distal end of the depth stop. Proximal and distal perpendicular surfaces 148 will precisely locate the distal end of the surgical or catheter device.

Figure 7:
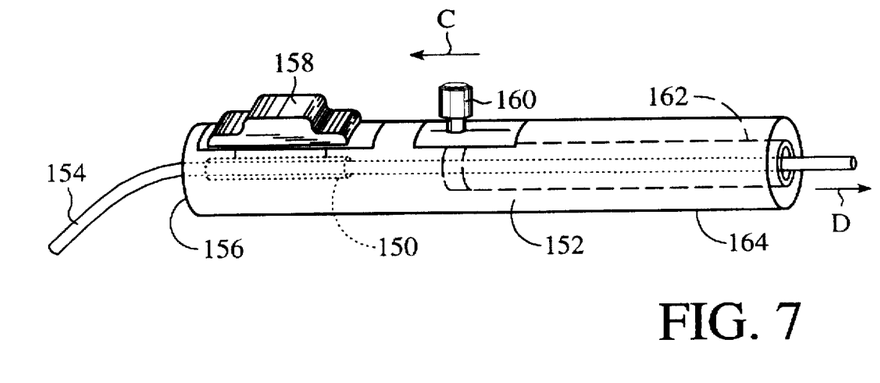
FIG. 7 is a schematic view of a preferred embodiment of a laser delivery means advancing and depth stop deploying mechanism of the present invention.

FIG. 7 is a schematic view of a preferred embodiment of a laser delivery means advancing mechanism 150 adjacent the outer lumen 152 of the surgical or catheter device of the present invention. The laser delivery means 154, such as a fiber optic cable or other waveguide, enters the surgical or catheter device at the proximal end 156 of the mechanism. An advance operator 158 is useful for advancing the laser delivery means into a predetermined position relative to the inner lumen, or the outer lumen, of the surgical or catheter device, depending upon the precise arrangement of the system.. A depth stop actuator lever 160 is easily manipulated by the surgeon. As the lever is moved in the direction C, the inner lumen 162 is moved in the same direction thus deploying the depth stop, e.g. a braided basket or moly protrusions. It will be understood that the outer lumen will extend from it's proximal end 164 over the inner lumen along the direction D.

Figure 8:
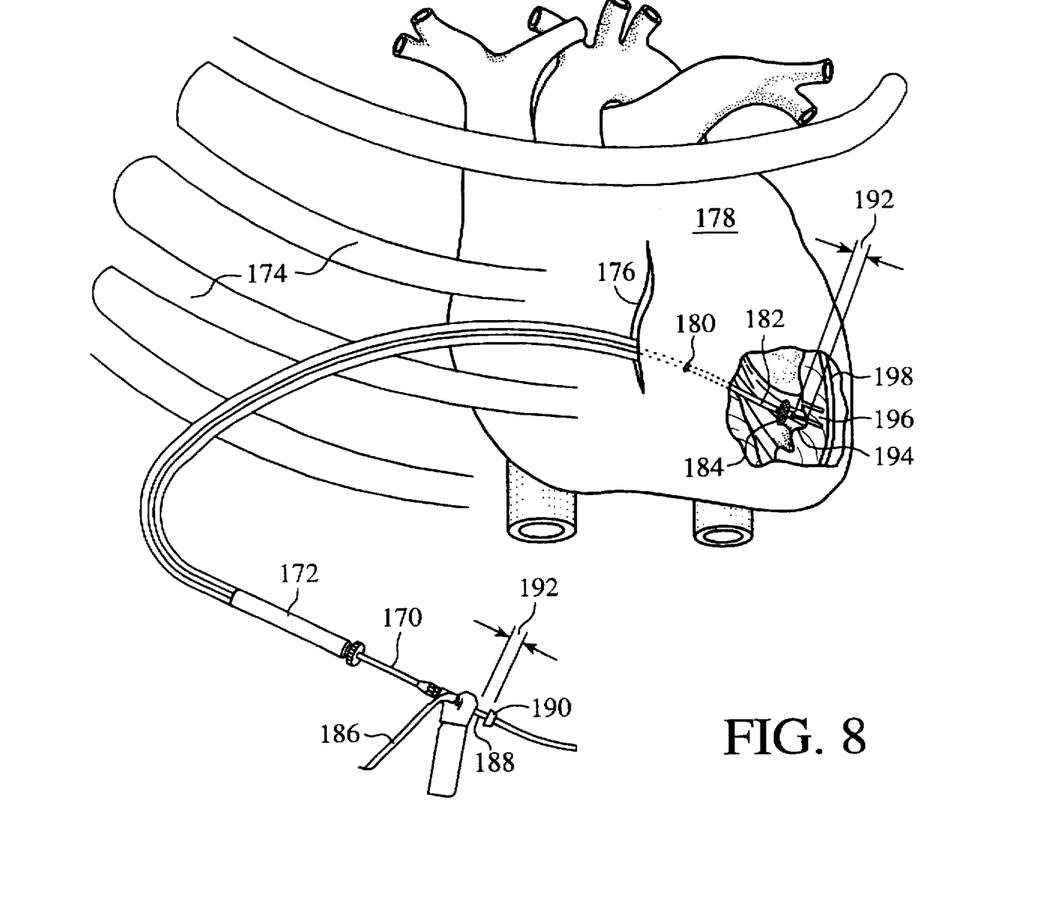
FIG. 8 is a schematic view demonstrating a preferred method of performing a TMR or other procedures using a preferred embodiment of a surgical or catheter device with depth stop device of the present invention.

FIG. 8 is a schematic view demonstrating a preferred method of performing a TMR or other procedure using a preferred embodiment of a surgical or catheter device with a depth stop device of the present invention. In FIG. 8, the surgical device 170 is passed through a thoracotomy, sternotomy or trocar device 172 positioned between the ribs 174 of the patient. The device is passed through an incision 176 in the pericardial sac 178 and up against an upward facing epicardial surface 180, most commonly of either the right or the left ventricle. The device is pushed through the epicardial surface by using laser energy or by mechanically piercing means to gain entrance to the ventricle or other organ chamber. Once the distal end 182 of the outer lumen of the surgical device is inside the organ chamber, the depth stop device 184 is deployed by deploying means 186. In this case, the deploying means is a hand-operated trigger which, when squeezed, retracts the inner lumen and axially compresses, while radially expanding, the depth device—either moly bolt wings, braided basket, balloon tip or other. The fiber or other laser delivery means 188 is advanced until the preset stop 190 is engaged. Thus, having set the predetermined exposed laser delivery means distance 192, the operator can create multiple holes through the endocardium 194, into the myocardium 196, but not into the protective epicardial layer 198. It will be understood that once the procedure is complete and the surgical device has been withdrawn from the internal chamber of the heart, the epicardial surface can be stitched shut easily with a pursestring-type suture or other means.

Figure 9:
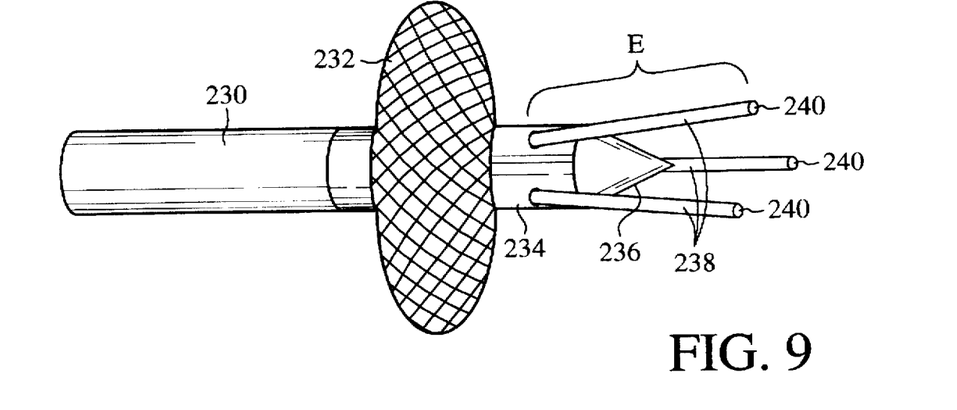
FIG. 9 is a schematic view of a preferred embodiment of a multi-laser delivery means surgical or catheter device of the present invention.

FIG. 9 is a schematic view of a preferred embodiment of a multi-laser delivery means surgical or catheter device of the present invention. The outer lumen 230 has a depth stop device 232 of the present invention disposed at it's distal end 234. Distal to the depth stop device, the extending pointed end 236 serves the function of piercing tissue to enter organ chambers or to precisely position the device on the outside surface of tissue or other matter. In the present embodiment, a plurality of laser delivery means 238 are shown extending a predetermined length E. With this device, laser energy can be simultaneously transmitted from the distal firing tips 240 of the plurality of laser delivery means. It will be understood that any number of laser delivery means, such as optical fibers or other waveguides, can be used.

Figure 10A:
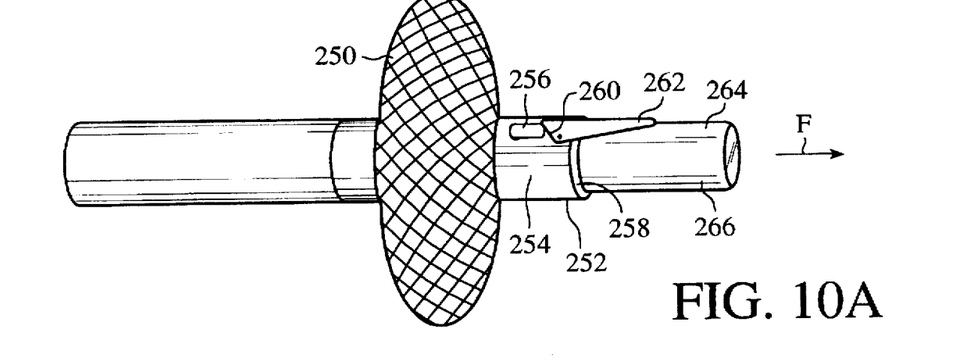
FIG. 10A is a schematic view of a preferred embodiment of a surgical or catheter device of the present invention with a laser delivery means firing tip orientation mechanical linkage.

FIG. 10A is a schematic view of a preferred embodiment of a surgical or catheter device of the present invention with a laser delivery means firing tip orientation mechanical linkage. This device also has a depth stop 250 and extending end portion 252 of an outer lumen 254. Inside the lumen there extends a control plunger 256 which terminates adjacent the distal end 258 of the outer lumen at a cam surface 260 on a mechanical linkage member 262. The distal end 264 of the laser delivery means 266, in one position, extends from the distal end of the lumen a short distance. Thus, in the figure shown, the laser energy will be directed in essentially the direction shown as F, with slight if any divergence.

Figure 10B:
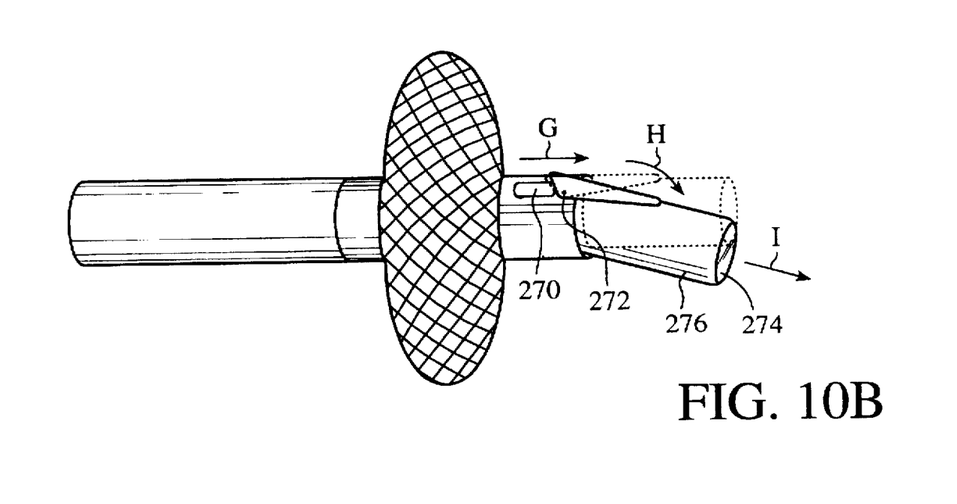
FIG. 10B is a schematic view of a preferred embodiment of a surgical or catheter device of the present invention with a laser delivery means firing tip orientation mechanical linkage in a deployed position.

FIG. 10B is a schematic view of a preferred embodiment of a surgical or catheter device of the present Invention with a laser delivery means firing tip orientation mechanical linkage in a deployed position. As the control plunger 270 is moved in the direction G, the mechanical linkage member, rotating about pivot point 272 in direction H. Therefore, the distal end 274 of the laser delivery means 276 will be directed slightly downward and delivering laser energy in essentially the direction shown by I. This ability to redirect the firing tip of the laser delivery means is key to the success of this embodiment of the present invention. Operation or manipulation of less-invasive surgical equipment through the narrow confines of a trocar or other similar device limits the operator's ability to angle the laser delivery means through an arc. This is not a concern or otherwise a problem with conventional open-chest or standard thoracotomies. It will be understood that there will be upper limits for the degree of bend which can be introduced into the distal end of the laser delivery means. Not only are optical fibers often brittle and not greatly flexible through a small radius, but advancement of the fiber or other waveguide through the surgical or catheter device is restricted when the mechanical linkage element is deployed.

The present invention is intended for use with any medical laser. In particular, the Holmium laser, including many of various different types known and available now or at any time, will be particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this application.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A catheter device with a depth stop device for tissue removal comprising:

a tissue removal device which has i) a proximal end adapted for coupling to an energy source and ii) a distal end that includes at least one member that effectuates tissue removal;

an outer sleeve which has a proximal end and a distal end, the outer sleeve defines a central axis of the catheter device;

an inner sleeve which has a distal end that attaches to the outer sleeve's distal end, the inner sleeve translates within the outer sleeve, and the tissue removal device's distal end axially translates within the inner sleeve; and the depth stop device which attaches to the outer sleeve's distal end section, the depth stop device is an annular member that slides on the inner sleeve, the annular member is axially compressible and radially expandable, the distal end of the outer sleeve has an extension beyond the depth stop member forming a stabilizing tissue contacting end portion for the catheter device;

thereby maintaining predetermined positioning of the catheter device's distal end relative to the tissue removal device.

2. The catheter device of claim 1 wherein the tissue removal device is a laser energy delivery device and the at least one member is an optical fiber.

3. The catheter device of claim 1 wherein the annular member is a cross-braided member and deployable from a surface contour substantially defined by the outer sleeve thereby obviating binding during catheter positioning.

4. The catheter device of claim 1 wherein the expandable annular member is a fluted member and deployable from a surface contour substantially defined by the outer sleeve thereby obviating binding during catheter positioning.

5. The catheter device of claim 1 wherein the stabilizing tissue contacting end portion is a tapered surface thereby enabling tissue penetration.

6. The catheter device of claim 1 wherein the stabilizing tissue contacting end portion is sharpened surface thereby enabling tissue penetration.

7. The catheter device of claim 1 wherein the outer sleeve is rigid.

8. The catheter device of claim 1 wherein the outer sleeve is flexible.

9. The catheter device of claim 1 further comprising a depth stop deploying mechanism for actively deploying the depth stop device wherein the distal ends of both the outer and the inner sleeves attach to the deploying mechanism and a proximal end of the catheter device includes a control means for deploying the depth stop device.

10. The catheter device of claim 1 wherein the stabilizing tissue contacting end portion has a plurality of openings that allow translation of distal endings of the tissue removal device formed by several members which are a plurality of optical fibers.

11. The catheter device of claim 1 further comprising a variable directional device for the tissue removal device at the catheter device's distal end, the variable directional device includes:

a plunger extending parallel to the central axis of the catheter device and through the outer sleeve, the plunger has a proximal end and a distal end; and a mechanical linkage element attaching to the distal end of the outer sleeve at an attachment point, the mechanical linkage element has a cam surface with a distally extending redirecting surface, whereby axial motions of the plunger through the outer sleeve causes the plunger's distal end to bear against the cam surface causing rotation of the mechanical linkage element about the attachment point between the mechanical linkage element and the distal end of the outer sleeve.

12. A catheter device with a depth stop device for removal of tissue comprising:

a tissue removal device which has i) a proximal end adapted for coupling to an energy source and ii) a distal end that includes at least one member that effectuates tissue removal;

an outer sleeve having a proximal end and a distal end, the outer sleeve defines a central axis of the catheter device, a distal end of the tissue removal device axially translates within the outer sleeve;

the depth stop device attaching to the outer sleeve's distal end section, the distal end of the outer sleeve has an extension beyond the depth stop device forming a stabilizing tissue contacting end portion for the catheter device, the depth stop device forming a compressible and radially expandable balloon member when deployed defines essentially a transverse tissue engaging surface area; and a depth stop deploying mechanism that includes a control means for expanding the balloon member, thereby maintaining predetermined positioning of the catheter device s distal end relative to the tissue removal device's distal end.

13. The catheter device of claim 12 wherein the tissue removal device is a laser energy delivery device and the at least one member is an optical fiber.

14. The catheter device of claim 12 wherein the outer sleeve is rigid.

15. The catheter device of claim 12 wherein the outer sleeve is flexible.

16. The catheter device of claim 12 wherein the stabilizing tissue contacting end portion has a plurality of openings that allow translation of distal endings of the tissue removal device formed by several members which are a plurality of optical fibers.

17. The catheter device of claim 12 further comprising a variable directional device for the tissue removal device at the catheter device's distal end, the variable directional device includes:

a plunger extending parallel to the central axis of the catheter device and through the outer sleeve, the plunger has a proximal end and a distal end; and a mechanical linkage element attaching to the distal end of the outer sleeve at an attachment point, the mechanical linkage element has a cam surface with a distally extending redirecting surface, whereby axial motions of the plunger through the outer sleeve causes the plunger's distal end to bear against the cam surface causing rotation of the mechanical linkage element about the attachment point between the mechanical linkage element and the distal end of the outer sleeve.

18. A method of using a catheter device with a depth stop for creating multiple myocardial revascularizing channels simultaneously in a heart comprising the steps of:

(a) positioning the distal end of a catheter device with depth stop adjacent target tissues;

(b) deploying the depth stop so as to maintain a precise spatial relationship between the catheter device and the target tissues;

(c) positioning a plurality of optical fibers from a catheter device with a distally extending tip portion extending axially past the depth stop, the distally extending tip portion having a plurality of openings such that the plurality of optical fibers extend through the catheter device's outer sleeve and can pass through the plurality of openings; and (d) delivering laser energy to the target tissues through the optical fibers.

19. The method of claim 18 wherein the step (d) of delivering laser energy to a portion of the heart for creating the multiple channels includes delivering sufficient laser energy to penetrate into the target tissue that is a predetermined distance through an endocardium without penetrating the epicardium.

20. The method of claim 18 wherein prior to step (d), the distally extending tip portion of the distal end of the catheter device is pushed into tissue adjacent to the target tissues.

21. The method of claim 18 wherein prior to step (d), distal ends of the optical fibers are pushed into the target tissue undergoing treatment.

22. The method of claim 18 further comprising a step of:

(e) delivering material to the target tissue, wherein the material is antibiotics to prevent infection, blood thinning agents, heart-function modifiers, visualization enhancing fluid or marker fluids.

23. The method of claim 18 wherein prior to step (a), the catheter device is inserted through a tube placed through a chest wall to reach an external surface of the human heart and the distal end of the catheter device is positioned on the heart during step (a).

24. The method of claim 18 wherein prior to step (a), the catheter device is placed through an external surface of the human heart so that the distal end of the catheter device is disposed inside the heart adjacent the distally located endocardial surface during step (a), the deployed depth stop mechanism of the catheter device is repositioned such that a contacting surface of the depth stop bears against the distally located endocardial surface of the heart chamber during step (b), and the channels created by the laser energy extend from the distally located endocardial surface of the heart chamber toward the outer surface of the heart through a portion of the myocardium during step (d).

25. The method of claim 18 wherein prior to step (a), the catheter device is vascularly inserted into the human heart so that the distal end of the catheter device is disposed inside a heart chamber adjacent the distally located endocardial surface during step (a), the deployed depth stop mechanism of the catheter device is repositioned such that a contacting surface of the depth stop bears against the distally located endocardial surface of the left ventricle chamber during step (b), and the channels created by the laser energy extend from the endocardial surface of the heart chamber toward the outer surface of the heart through a portion of the myocardium during step (d).

* * * * *